United States Patent [19]

Benson

[11] Patent Number: 5,344,404
[45] Date of Patent: Sep. 6, 1994

[54] SYRINGE ASSEMBLY HAVING A NON-RESUABLE NEEDLE SHIELD

[75] Inventor: Carl L. Benson, Wyckoff, N.J.

[73] Assignee: Becton, Dickinson and Company, Franklin Lakes, N.J.

[21] Appl. No.: 105,700

[22] Filed: Aug. 13, 1993

[51] Int. Cl.⁵ ............................................. A61M 5/00
[52] U.S. Cl. ................................... 604/110; 604/192
[58] Field of Search ............ 604/192, 187, 110, 111, 604/263; 206/364, 365

[56] References Cited

U.S. PATENT DOCUMENTS

| | | | |
|---|---|---|---|
| 4,559,042 | 12/1985 | Votel | 604/192 |
| 4,573,975 | 3/1986 | Frist et al. | 604/192 |
| 4,717,386 | 1/1988 | Simmons | 604/192 |
| 4,740,204 | 4/1988 | Masters et al. | 604/192 |
| 4,781,697 | 11/1988 | Slaughter | 604/192 |
| 4,799,927 | 1/1989 | Davis et al. | 604/192 |
| 4,886,497 | 12/1989 | Scholl, Jr. | 604/111 |
| 4,892,525 | 1/1990 | Hermann, Jr. et al. | 604/263 |
| 4,900,309 | 2/1990 | Netherton et al. | 604/192 |
| 4,906,235 | 3/1990 | Roberts | 604/192 |
| 4,909,792 | 3/1990 | Norelli | 604/263 X |
| 4,919,656 | 4/1990 | Bracker et al. | 604/192 |
| 4,950,249 | 8/1990 | Jagger | 604/192 |
| 4,966,591 | 10/1990 | Yuen | 206/365 X |
| 4,986,817 | 1/1991 | Code | 604/192 |
| 5,002,536 | 3/1991 | Thompson et al. | 604/192 |
| 5,021,049 | 6/1991 | Howard | 604/192 |
| 5,190,532 | 3/1993 | Yu | 604/192 |

Primary Examiner—John D. Yasko
Attorney, Agent, or Firm—John L. Voellmicke

[57] ABSTRACT

A syringe assembly having a non-reusable needle shield includes an elongate barrel having a chamber for retaining fluid, an open proximal end and a closed distal end. A tip extends from the distal end and includes a passageway therethrough in fluid communication with the chamber. A needle cannula extends distally from the tip. The cannula includes a lumen therethrough in fluid communication with the passageway. An elongate hollow needle shield having a longitudinal axis, a distal end and an open proximal end is positioned on the barrel tip so that the tip extends into the open proximal end of the shield and the shield covers the needle cannula. The needle shield is divided along the longitudinal axis into a plurality of separate needle shield segments. Frangible structure is provided for releasably holding the needle shield segments together and preventing removal of the needle shield from the syringe assembly. Disengagement of the frangible means allows the needle shield segments to separate and come apart to expose the needle cannula and after disengagement, the needle shield segments can no longer by themselves engage the tip of the barrel to shield the needle cannula.

12 Claims, 7 Drawing Sheets

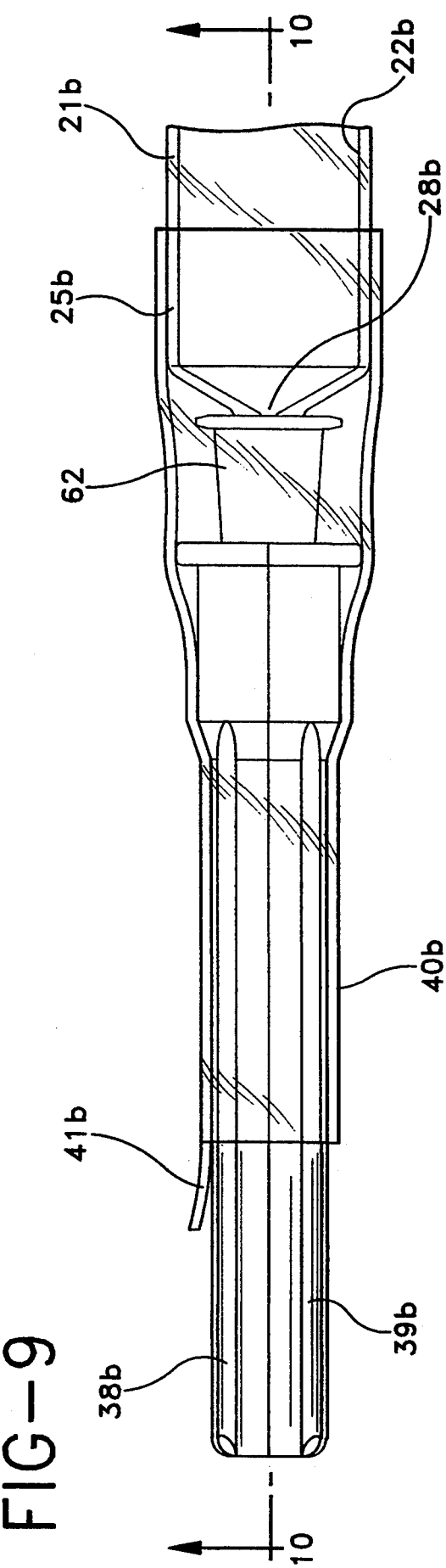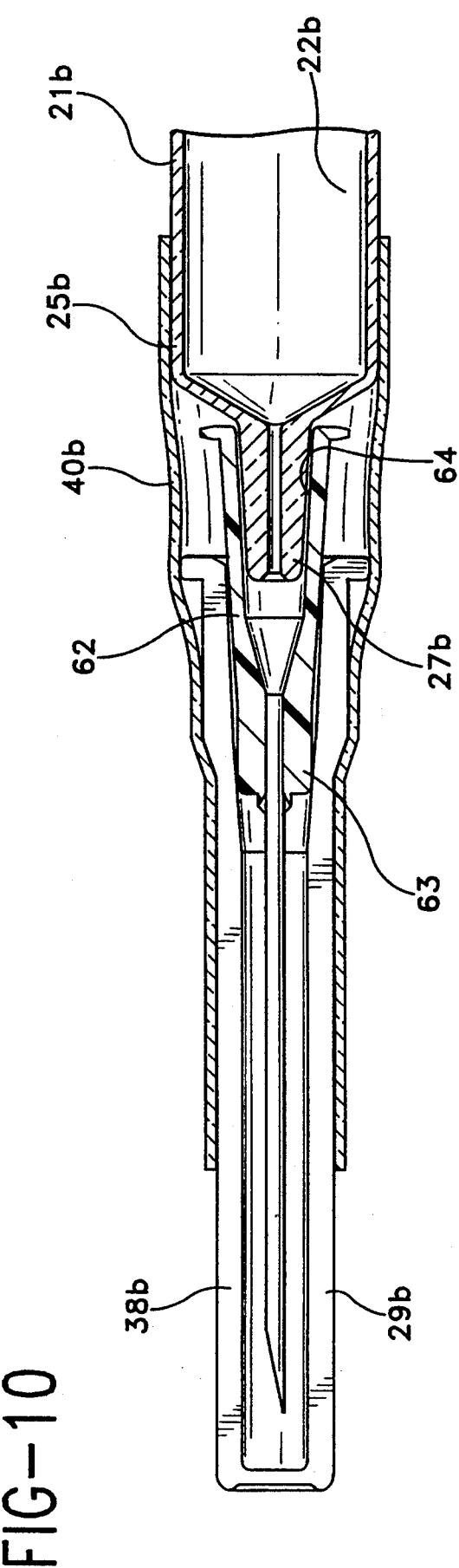

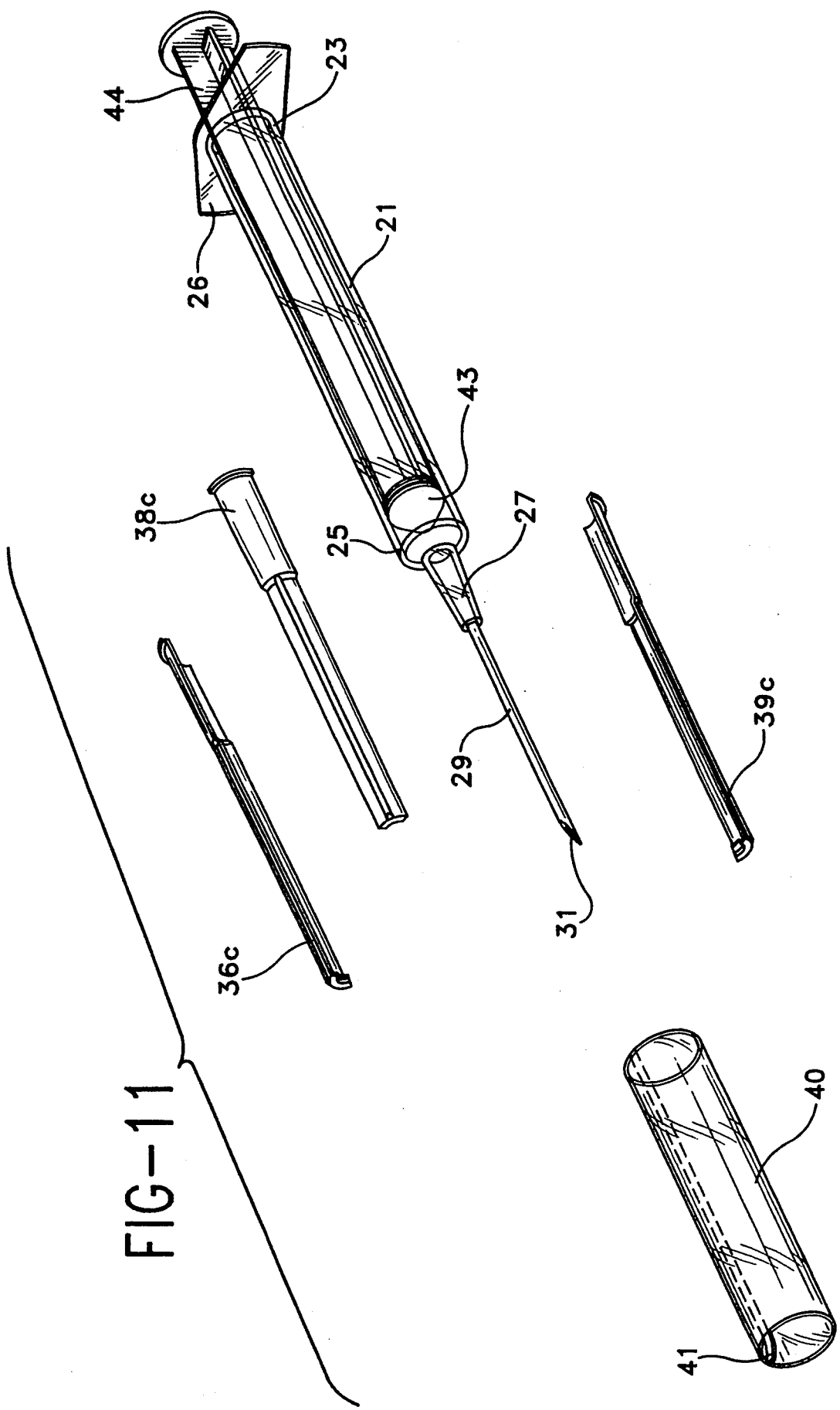

SYRINGE ASSEMBLY HAVING A NON-RESUABLE NEEDLE SHIELD

BACKGROUND OF THE INVENTION

1. Field of the Invention.

The present invention relates to syringes and more particularly concerns disposable syringes having non-reusable needle shields.

2. Description of Related Information.

Generally speaking, a hypodermic syringe consists of a cylindrical barrel, most commonly made of plastic or glass, with a distal end containing a hypodermic needle or adapted to be connected to a hypodermic needle and a proximal end adapted to receive the stopper in a plunger rod assembly. The distal end of the barrel or the needle assembly usually includes a needle shield which removably covers the needle to prevent damage to the needle before use and to prevent accidental needle sticks.

At the time of use, the needle shield is removed exposing the sharp point of the needle cannula. Even before use, the sharp point of the needle can inflict minor injury if the user inadvertently sticks himself or herself. After use, the sharpened needle tip poses an additional risk because it may be contaminated and be an instrument for the inadvertent transfer of infection or disease.

Great effort has been expended to minimize the possibility of inadvertent needle sticks. Inadvertent needle sticks can happen during the act of reshielding as the user attempts to guide the sharp needle into the small diameter proximal open end of the needle shield so that the needle shield re-engages the hub or syringe tip. The user may miss the needle shield and stick his or her own hand. It is the belief of some that needle reshielding should not be attempted and the used hypodermic syringe and needle should be disposed of immediately after use in a sharps collecting device. U.S. Pat. No. 4,717,386 teaches a device for uncapping and capping the protective sheath of a hypodermic needle. In one embodiment, a hand-held shield is provided to isolate the fingers from the sheath and to provide a barrier to protect the user in case the needle misses the opening in the sheath upon reassembly. Reshielding devices such as this must be carefully designed and carefully used. The shield material must be strong enough to prevent the needle from penetrating all the way through to the user's hands yet not hard enough so that the needle will slide off the shield into the user's hand. Although this type of device greatly reduces the chance of needle sticks, it does not eliminate it. There are many needle shields in the prior art which are designed with enlarged proximal ends to help shield the user's hand in case the needle is not properly placed back into the cavity of the needle shield. These devices all reduce the risk of accidental needle stick but do not prevent it.

All risk of accidental needle stick caused by reshielding could be eliminated by a syringe having a needle shield structure which, when the needle shield was removed, could not be replaced. There is a need for a simple, straight-forward, reliable, easily fabricated device syringe having a needle shield which cannot be reinstalled over the needle after its removal.

SUMMARY OF THE INVENTION

A syringe assembly having a non-reusable needle shield of the present invention includes an elongate barrel having a chamber for retaining fluid. The barrel includes an open proximal end, a closed distal end and a tip extending from the distal end having a passageway therethrough in fluid communication with the chamber. A needle cannula extends distally from the barrel tip. The cannula includes a lumen therethrough in fluid communication with the passageway. An elongate hollow needle shield having a longitudinal axis, a distal end and an open proximal end is provided. The shield is positioned on the tip so that the tip extends into the open end of the shield and the shield covers the needle cannula. The needle shield is divided along its longitudinal axis into a plurality of separate elongate needle shield segments. Frangible means for releasably holding the needle shield segments together and preventing removal of the needle shield from the syringe assembly is provided. Frangible means may include plastic shrink wrap, injection molded collars having areas of reduced strength to allow tearing the collar apart through the use of an extended tab, or other frangible structures including those molded into the needle shield segments. Disengagement of frangible means allows the needle shield segments to separate and come apart to expose the needle cannula. After disengagement, the needle shield segments can no longer, by themselves, engage the tip of the barrel to shield the needle cannula.

BRIEF DESCRIPTION OF THE DRAWINGS

FIG. 9 is a partial side elevation view of still another alternative embodiment of the present invention.

FIG. 10 is a cross-sectional view of the syringe assembly of FIG. 9 taken along lines 10—10.

FIG. 11 is an exploded perspective view illustrating an alternative embodiment of the syringe of the present invention with the sleeve and three needle shield elements in position for assembly.

DETAILED DESCRIPTION

Figure 1:
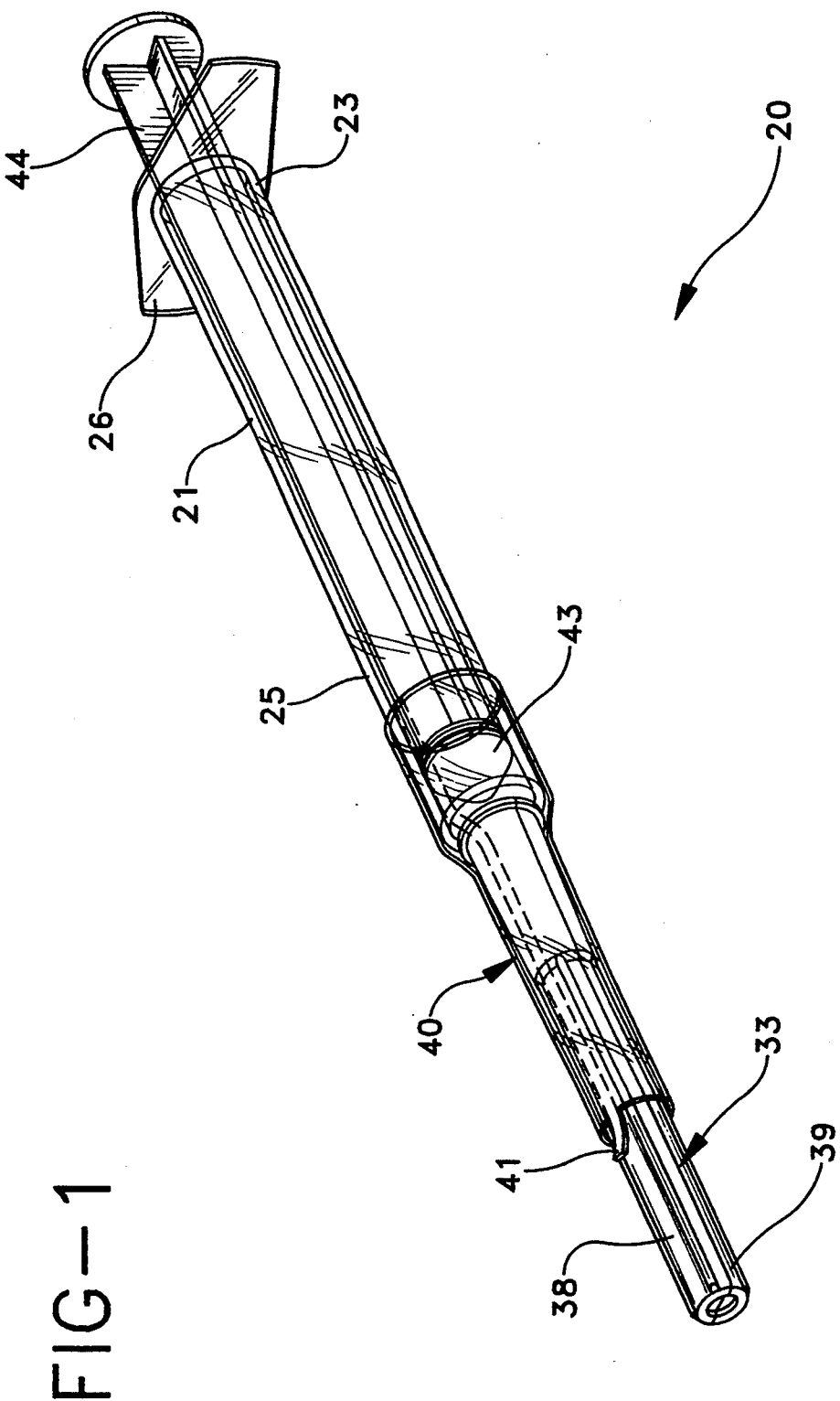
FIG. 1 is a perspective view of the syringe of the present invention.
Figure 2:
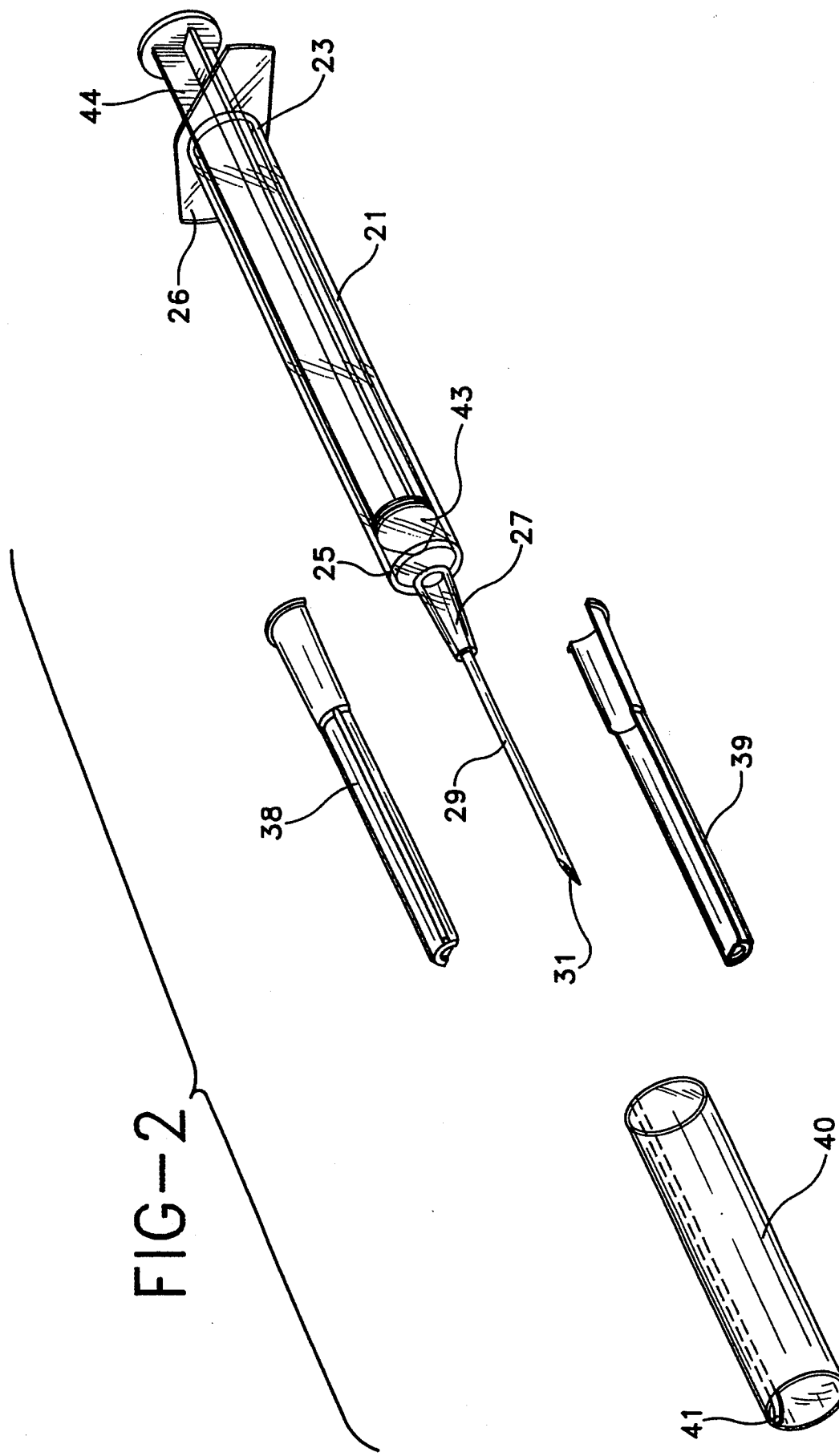
FIG. 2 is an exploded perspective view illustrating the syringe of the present invention with the sleeve and needle shield in position for assembly.

While this invention is satisfied by embodiments in many different forms, there are shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1–6, a syringe assembly 20, having a non-reusable needle shield, includes an elongate barrel 21 having a chamber 22 for retaining fluid. Barrel 21 includes an open proximal end 23, a closed distal end 25 and a tip 27 extending from said distal end and having a passageway 28 therethrough in fluid communication with chamber 22. A needle cannula 29 having a sharpened distal tip 31 and a lumen therethrough in fluid communication with passageway 28. The needle cannula projects outwardly from distal end 25 of the barrel. The syringe in this embodiment includes a needle cannula which is attached directly to the distal end of the barrel using adhesives or other suitable means. It is within the purview of the present invention to include a syringe having a needle cannula which is attached to a hub which frictionally engages a syringe tip. Such an embodiment is described hereinafter.

For the purposes of the description of the present invention, the term "distal end" is meant to refer to the end furthest from the person holding the syringe and closest to the needle, whereas the term "proximal end" is meant to refer to the end closest to the holder of the syringe.

An elongate hollow needle shield 33 defines a longitudinal axis 34 and includes distal end 35 and open proximal end 37. The needle shield is positioned on barrel tip 27 so that the tip extends into the open proximal end of the needle shield and the needle shield covers the needle cannula. The needle shield is divided along longitudinal axis 34 into a plurality of separate elongate needle shield segments. In this embodiment there are two needle shield segments indicated as 38 and 39. In this embodiment elements 38 and 39 can be identical parts. Also, the mating surfaces of the needle shield segments can be flat as indicated by numeral 40 or the surface can be irregular such as, "V" shaped to cause the two halves to mate together to form a round concentric cavity for receiving the needle cannula. Three or more needle shield, as illustrated in FIG. 11, segments are also within the purview of this invention.

Figure 3:
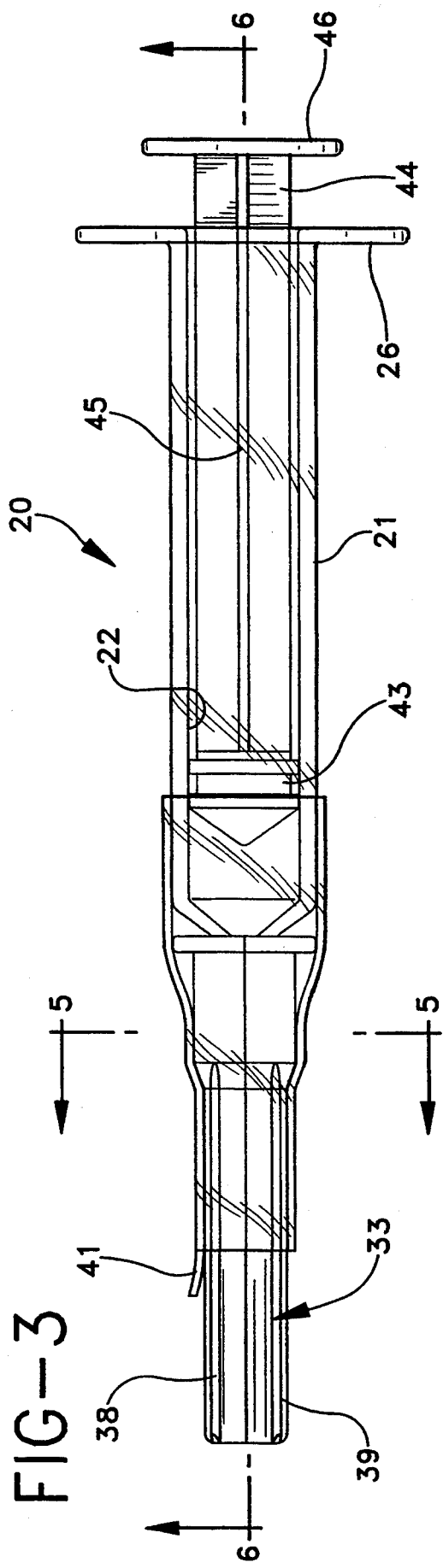
FIG. 3 is a side elevation view of the syringe of FIG. 1.
Figure 5:
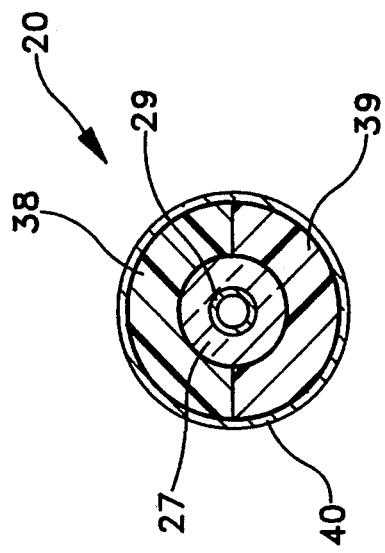
FIG. 5 is a cross-sectional view of the syringe assembly of FIG. 3 taken along lines 5—5.
Figure 4:
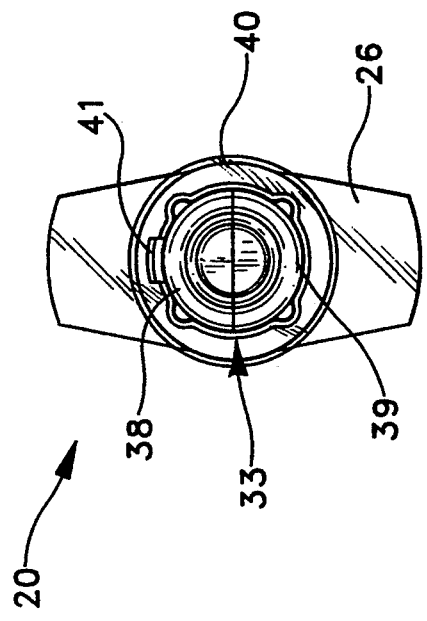
FIG. 4 is a side elevation view of the distal end of the syringe of FIG. 3.
Figure 6:
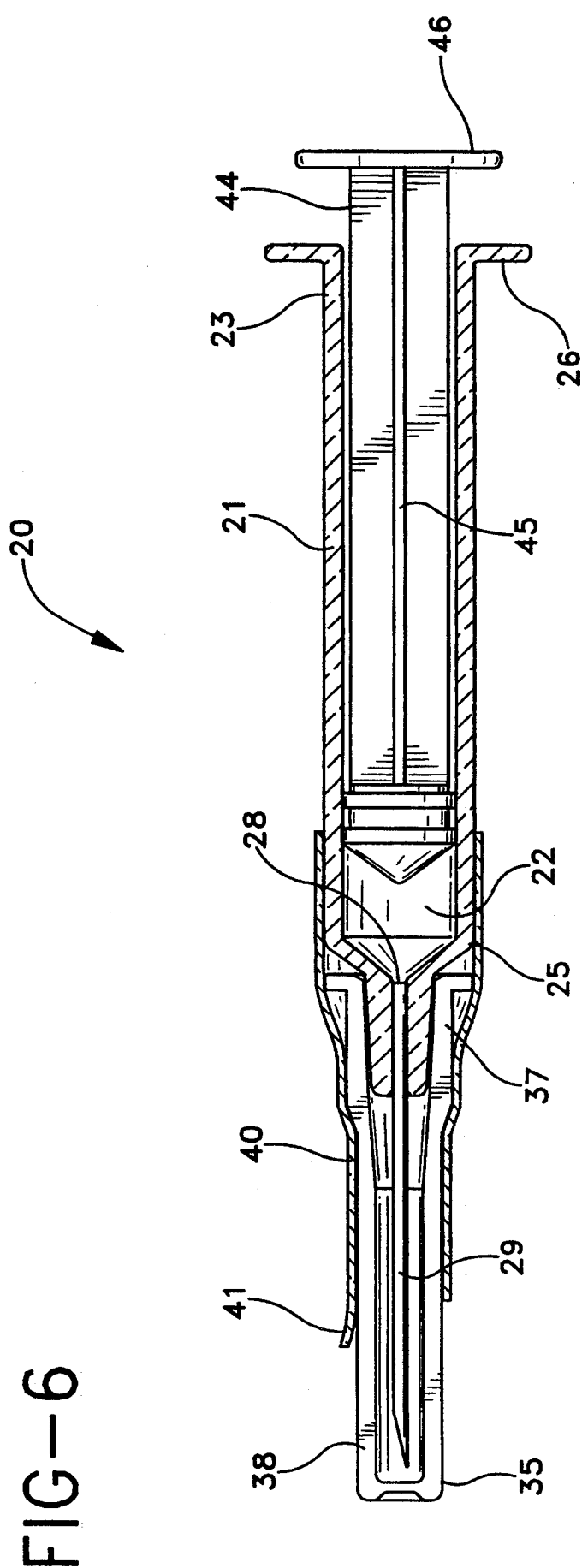
FIG. 6 is a partial cross-sectional view of the syringe of FIG. 3 taken along line 6—6.

It is apparent that the needle shield, as described hereinabove, cannot maintain itself on the barrel tip without the application of an outside force to hold the needle shield segments 38 and 39 together sufficiently tightly to create a frictional engagement of the interior surface of the open proximal end of the needle shield with the barrel tip. To this end, the present invention includes frangible means for releasably holding the needle shield segments together. In this preferred embodiment, the frangible means is a cylindrically shaped plastic shrink-wrap sleeve 40. The sleeve performs two functions. First, it holds the needle shield segments together tightly for engaging the barrel tip and, second, it provides further structure to hold the needle shield to the barrel. During assembly, the two needle shield segments are held together to form a needle shield and the needle shield is engaged the syringe barrel as illustrated in FIGS. 1, 3 and 6. Sleeve 40 is placed along the barrel and the needle shield as illustrated and is shrunk using known methods so that it tightly grasps the needle shield holding the needle shield segments together and providing additional force to hold the now unitary needle shield onto the barrel. Sleeve 40 also includes tear tab to facilitate tearing the shrink wrap sleeve to release the needle shield from the syringe barrel. Tearing the sleeve allows the needle shield segments to separate and come apart to expose the needle cannula. After disengagement, the needle shield segments can no longer by themselves engage the tip of the syringe barrel to shield the needle cannula as they become two or more separate pieces which do not and cannot by themselves, function as a needle shield. Thus, the use of the present invention prevents reshielding of a previously exposed used hypodermic needle and therefor eliminates the risk of accidental needle stick and the subsequent injuries and negative consequences resulting therefrom. The use of the present invention removes the discretion of the user to reshield. The user can no longer reshield and thus the hospital and institutional policies against reshielding are assured to be carried out.

This embodiment of the present invention also includes a stopper 43 slidably positioned in fluid-tight engagement inside barrel 21. The stopper is capable of moving fluid from chamber 22 through passageway 28 upon its movement toward distal end 25 of the barrel. The stopper is also capable of facilitating the drawing of fluid into the chamber through the passageway upon its movement away from distal end 25 of the barrel. A plunger rod 44 having an elongate body portion 45 engages stopper 43 to facilitate operation of the stopper. Body portion 45 extends outwardly from open proximal end 23 of the barrel. Disc-shaped plunger rod flange 46 is provided as a convenient structure for applying force to the plunger rod with respect to the barrel. A flange 26 is also provided at the proximal end of the barrel to facilitate handling and positioning the syringe assembly and for maintaining the relative position of the barrel with respect to the plunger rod during filling and medication administration.

In use, the syringe assembly of the present invention is held by the user. With one hand holding the syringe barrel, the other hand is used to pull tear tab 41 in a proximal direction, to tear sleeve 40 in an axial direction along its entire axial length. At this time, the needle shield segments should fall off of the syringe barrel or be easily removed therefrom with minimal, carefully applied digital force. Now, the syringe assembly with exposed needle, can be used in known ways to deliver medication to a patient, or for other known purposes.

Figure 7:
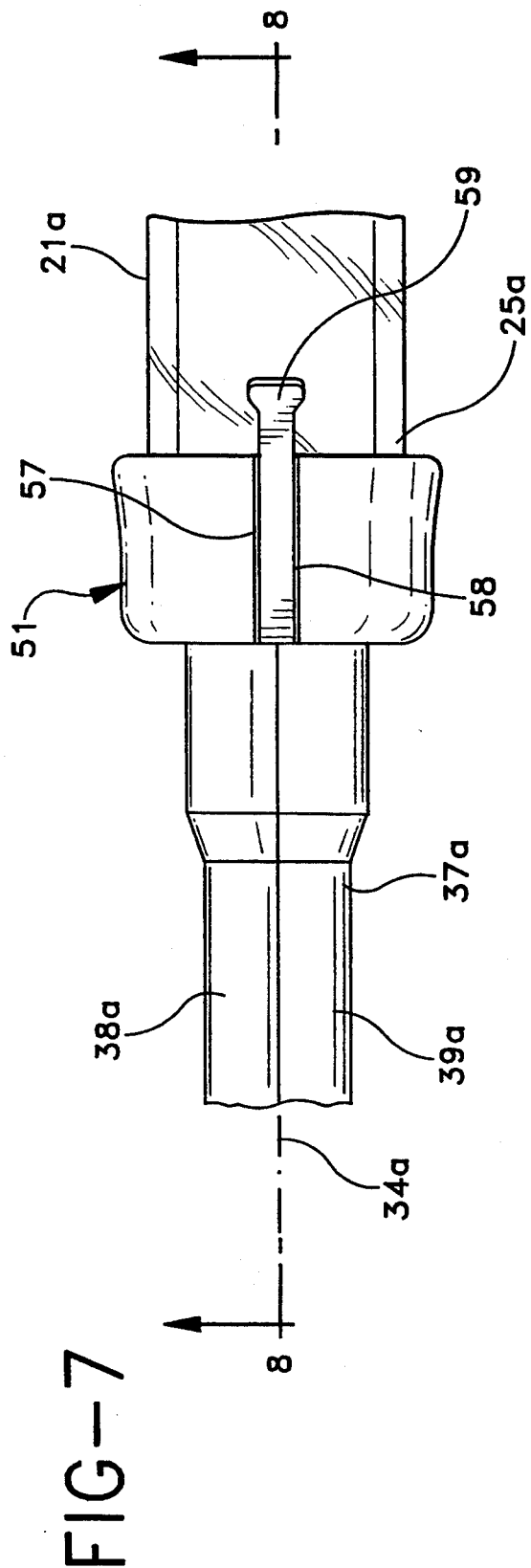
FIG. 7 is an enlarged partial side elevation view of an alternative embodiment of the present invention.
Figure 8:
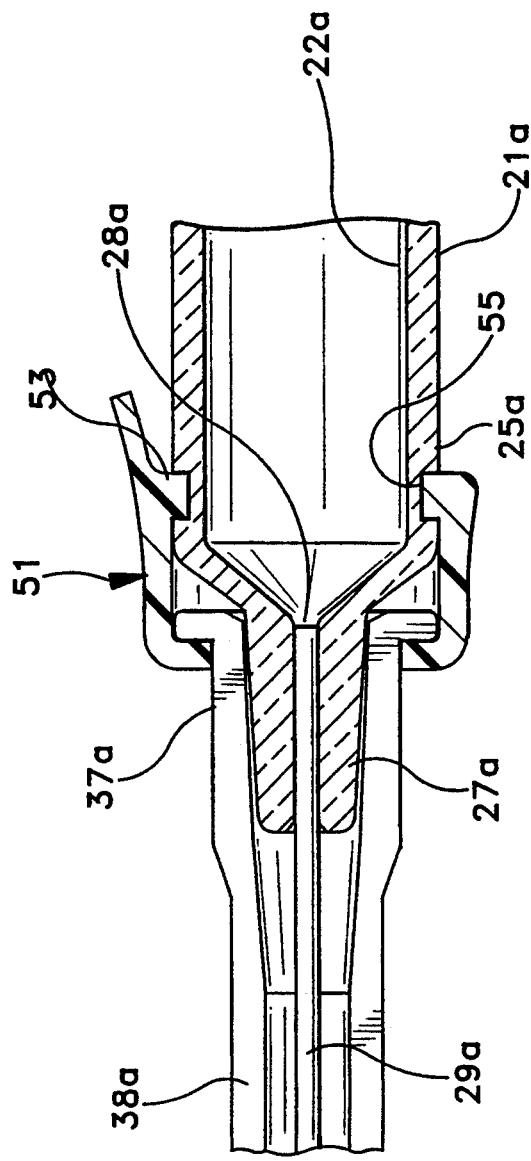
FIG. 8 is a cross-sectional view of the syringe assembly of FIG. 7 taken along lines 8—8.

Referring now to FIGS. 7 and 8, an alternative embodiment of the syringe assembly of the present invention is illustrated. In this alternative embodiment, the structure of the syringe assembly is substantially similar to the syringe assembly of FIGS. 1–6. Accordingly, substantially similar components perform substantially similar functions will be numbered identically to those components of the embodiment of FIGS. 1–6 except a suffix "a" will be used to identify these components in FIGS. 7 and 8.

Alternative syringe assembly 50 includes elongate barrel 21a having a chamber 22a for retaining fluid. The barrel includes distal end 25a including a tip 27a having a passageway 28a therethrough in fluid communication with chamber 22a. A needle cannula 29a extends distally from the barrel tip and includes a lumen therethrough in fluid communication with passageway 28a. An elongate hollow needle shield 33a defines a longitudinal axis 34a and includes open proximal end 37a. The needle shield is divided along its longitudinal axis into two separate elongate needle shield segments 38a and 39a. Frangible means for releasably holding the needle shield segments together and for preventing removal of the needle shield from the syringe assembly includes frangible collar 51. The frangible collar includes distal inwardly projecting annular flange 52 which holds needle shield segments 38a and 39a together. The frangible collar also includes proximally located inwardly directed annular flange 53 which holds the collar in a fixed position with respect to the barrel. In this embodiment, the barrel desirably includes exterior annular groove 55 which engages proximal flange 53 to enhance the integrity of the assembly. Frangible collar 51 further includes score lines 57 and 58 which are formed in the collar to substantially reduce the cross-section area of the collar along the score lines. In use, the user may remove the needle shield by grasping tear tab 59 on frangible collar 51 and pulling the tear tab in a distal direction to shear score lines 57 and/or 58 causing the collar's grip on the needle shield segments and the barrel to be reduced to zero or a negligible force. At this time, carefully applied digital force will allow the collar and the needle shield segments to be removed.

Referring to FIGS. 9 and 10, another alternative embodiment of the present invention is illustrated. In this alternative embodiment the structure of the syringe assembly is substantially similar to the syringe assembly of FIGS. 1-6. Accordingly, substantially similar components that perform substantially similar functions will be numbered identically to those components of the embodiment of FIGS. 1-6 except a suffix "b" will be used to identify the components of FIGS. 9 and 10.

Alternative syringe assembly 62 includes an elongate barrel 21b having a chamber 22b for retaining fluid. The barrel includes distal end 25b and a tip 27b extending from the distal end and having a passageway 28b therethrough. A needle cannula 29b is attached to a hub 62 so that the proximal end of the needle 29b is connected to distal end 63 of the hub. Hub 62 includes a cavity 64 having a frusto-conically shaped interior surface which is adapted to frictionally engage tip 27b of the barrel in an arrangement that allows fluid communication between the lumen of the needle cannula and the chamber of the barrel through the cavity. In this embodiment, needle shield 33b includes segments 38b and 39b. In this embodiment, the needle shield engages the tip through the hub and the segments of the needle shield are held together and prevent it from being removed from the barrel through shrink wrap sleeve 40b. This embodiment illustrates that the present invention applies to syringe assemblies having needle cannula connected to a hub to form the needle assembly which frictionally engages the syringe barrel, and syringe assemblies where the needle is attached directly to the barrel without the use of a hub.

Referring to FIG. 11, another embodiment of the present invention is illustrated. In this alternative embodiment the structure of the syringe assembly is substantially similar to the syringe assembly of FIGS. 1-6. Accordingly, substantially similar components that perform substantially similar functions will be numbered identically to those components of the embodiments of FIGS. 1-6. The main difference between the embodiment of FIG. 11 and the embodiment of FIGS. 1-6 is that in the embodiment of FIG. 11, there are three needle shield segments indicated as 36c, 38c and 39c.

It is also within the purview of the present invention to include having the frangible means integrally molded with the needle shield segments so that, for example, the tear tab would project directly from the needle shield and pulling the tear tab would cause it to run along a portion of the needle shield segments to separate them from each other. Such a tab would be oriented so that the user would pull the tab toward the proximal end of the barrel away from the needle, to avoid accidental needle sticks while severing the connection between the segments of the needle shield.

The syringe barrel of the present invention may be constructed of a wide variety of materials such as plastic and glass with thermoplastic materials such as polypropylene and polyethylene being preferred. The needle shield of the present invention can also be constructed of a wide variety of rigid materials with thermoplastic materials being preferred.

Thus it can be seen that the present invention provides a simple, straight-forward, reliable, easily fabricated, syringe assembly having a non-reusable needle shield for substantially eliminating potential for accidental needle sticks caused by attempted reshielding procedures.

What is claimed is:

1. A syringe assembly having a non-reusable needle shield comprising:
   an elongate barrel having a chamber for retaining fluid, said barrel including an open proximal end, a closed distal end and a tip extending from said distal end having a passageway therethrough in fluid communication with said chamber;
   a needle cannula extending distally from said tip, said cannula having a lumen therethrough in fluid communication with said passageway;
   an elongate hollow needle shield having a longitudinal axis, a distal end and an open proximal end, said shield being positioned on said tip so that said tip extends into said open end of said shield and said shield covers said needle cannula, said needle shield being divided along said longitudinal axis into at least two separate elongate needle shield segments;
   frangible means for releasably holding said needle shield segments together and preventing removal of said needle shield from said syringe assembly, wherein disengagement of said frangible means allows said needle shield segments to separate and come apart to expose said needle cannula and after disengagement said needle shield segments no longer by themselves engage said tip to shield said needle cannula.

2. The syringe assembly of claim 1 wherein said needle shield comprises two needle shield segments.

3. The syringe assembly of claim 1 wherein said needle shield comprises at least three needle shield segments.

4. The syringe assembly of claim 1 wherein said needle shield segments have side walls running substantially parallel to said longitudinal axis, said side walls of adjacent needle shield segments contacting each other.

5. The syringe assembly of claim 1 wherein said frangible means includes a plastic shrink wrap film surrounding portions of said distal end of said barrel and said proximal end of said needle shield.

6. The syringe assembly of claim 1 wherein said frangible means includes a circulatory shaped plastic collar surrounding portions of said distal end of said barrel and said proximal end of said needle shield.

7. The syringe assembly of claim 1 wherein said needle shield is made of thermoplastic material and said frangible means is integrally molded with said needle shield segments.

8. The syringe assembly of claim 1 further including a hub attached to said proximal end of said needle cannula, said hub having an open proximal end and a cavity therein having an interior surface which frictionally engages said tip to hold said needle on said barrel so that said lumen is in fluid communication with said passageway.

9. The syringe assembly of claim 8 wherein said needle shield engages said barrel tip through said hub.

10. The syringe assembly of claim 1 further including a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end; and a plunger rod having an elongate body portion engaging said stopper to facilitate operation of said stopper, said body portion extending outwardly from said proximal end of said barrel to form a syringe assembly.

11. The syringe assembly of claim 1 wherein said needle shield is made of thermoplastic material.

12. The syringe assembly of claim 1 wherein said barrel is made of material selected from the group of polyethylene, polypropylene and glass.

* * * * *